US006348331B1

(12) United States Patent
Raymond

(10) Patent No.: US 6,348,331 B1
(45) Date of Patent: Feb. 19, 2002

(54) PICHIA METHANOLICA GLYCERALDEHYDE-3-PHOSPHATE DEHYDROGENASE 2 PROMOTER

(75) Inventor: Christopher K. Raymond, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/653,403

(22) Filed: Sep. 1, 2000

Related U.S. Application Data

(60) Provisional application No. 60/152,744, filed on Sep. 8, 1999.

(51) Int. Cl.[7] .......................... C07H 21/04; C12N 1/19; C12N 15/81; C12N 15/63
(52) U.S. Cl. ................... 435/69.1; 435/254.23; 435/320.1; 536/23.1; 536/24.1; 536/24.2
(58) Field of Search .............................. 536/23.1, 24.1, 536/24.2; 435/320.1, 254.23, 471, 69.1; 530/402

(56) References Cited

U.S. PATENT DOCUMENTS 6,153,424 A    11/2000   Raymond et al. ...... 435/254.23

FOREIGN PATENT DOCUMENTS

| WO | 97/17450 | 5/1997 |
|---|---|---|
| WO | 99/14320 | 3/1999 |
| WO | 00/56903 | 9/2000 |

OTHER PUBLICATIONS

Rosenberg et al., *Methods in Enzymology* 185:341–351, 1990.

Waterham et al., *Gene* 186:37–44, 1997.

*Primary Examiner*—John L. LeGuyader
*Assistant Examiner*—Lauren Nguyen
(74) *Attorney, Agent, or Firm*—Gary E. Parker

(57) ABSTRACT

Transcription promoter and terminator sequences from the *Pichia methanolica* glyceraldehyde-3-phosphate dehydrogenase 2 gene (GAP2 gene) are disclosed. The sequences are useful within DNA constructs for the production of proteins of interest in cultured *P. methanolica* cells. Within the expression vectors, a GAP2 promoter and/or a GAP2 terminator is operably linked to a DNA segment encoding the protein of interest.

19 Claims, No Drawings

SEQUENCE LISTING

```
<160> NUMBER OF SEQ ID NOS: 22

<210> SEQ ID NO 1
<211> LENGTH: 3333
<212> TYPE: DNA
<213> ORGANISM: Pichia methanolica
<220> FEATURE:
<221> NAME/KEY: CDS
<222> LOCATION: (1093)...(2094)

<400> SEQUENCE: 1
cataaaccat aatagtataa tttgttagac aagttcaaag aatttccaat aaaagtgtaa      60
ttttcacatg catttcaacc cggagaataa aattttaaga aatccgattg gatagtgtag     120
aattattgtt catattgtgt tataataatt gcaattaccc aacaaaactt gcattggtta     180
gtcatcgtat ttcatgctat tagctgaaag tagggtaatc gagcggtttg aatggctctg     240
taaatctaaa ctctttatct gaaatgtata ttagatccga catgatgcat ttggaggttc     300
tgagaggtac cgcattgaat ttctgtgtgg aattagatga gttgttgtac cagaagaggg     360
aaaatgggca agtggtggca atagtaaatt atgggaagta tggtggatat tggcccggcg     420
tagtgacatc ctcaccttaa aattgcctta ggggataatg tgccgggcac gtccagctaa     480
ctaatttagt agtcgtctaa aactggggaa catttgttgt tcctttgata gttatacgaa     540
actgattgaa taaaagttt atattcttct tgatgatcct tctgtctaat tgatagaata     600
ggaatttaga tagaaatatg gaaatacaca aaatatatgt aataaaatca aaggggaac     660 aattcaaagg attcagcaat caaaagggat gagtgattct gggtaataaa tgagcaataa     720
attagtaata aattagtaac aagttagtaa taaattagta ataaattagc aacaaatgaa     780
caatagtaaa agctaaaaga taaaacaaaa ggtaggagat aagcagtaaa gtccgaaagt     840
aatcaggtga ctagagtaag gatgagaatg aaggacagat tccttacagc tacataagta     900
gatgagctgt tgacggtcag atggtgcctt ggtccatggt ttcatatata aagaccctct     960
tcgtctcctt ttgttcgctt gtttcacact caactgtttc tgattttacc tttttttcccc    1020
```

```
tgcttgattc ccccattgaa tcagatcaag tgttttcata gaacccactt ttatttattt    1080
tagttgcaca aa atg gcc att aac gtt ggt att aac ggt ttc ggg aga atc    1131
          Met Ala Ile Asn Val Gly Ile Asn Gly Phe Gly Arg Ile
           1               5                  10 ggc aga tta gtc ttg aga gtt gcc tta tcg aga aaa gac atc aac gtc     1179
Gly Arg Leu Val Leu Arg Val Ala Leu Ser Arg Lys Asp Ile Asn Val
 15              20                  25 gtt gct gtc aac gat cct ttc att gct cct gat tac gct gct tac atg    1227
Val Ala Val Asn Asp Pro Phe Ile Ala Pro Asp Tyr Ala Ala Tyr Met
 30              35                  40                  45 ttc aag tac gat tcc act cac ggt aag tac act ggt gaa gtt tca agt    1275
Phe Lys Tyr Asp Ser Thr His Gly Lys Tyr Thr Gly Glu Val Ser Ser
                 50                  55                  60 gat ggt aaa tac tta atc att gat ggt aag aag att gaa gtt ttc caa    1323
Asp Gly Lys Tyr Leu Ile Ile Asp Gly Lys Lys Ile Glu Val Phe Gln
                 65                  70                  75 gaa aga gat cca gcc aac atc cca tgg ggg aaa gaa ggt gtt cag tac    1371
Glu Arg Asp Pro Ala Asn Ile Pro Trp Gly Lys Glu Gly Val Gln Tyr
             80                  85                  90 gtt att gaa tcc act ggc gtt ttc acc acc ttg gct ggt gct caa aag    1419
Val Ile Glu Ser Thr Gly Val Phe Thr Thr Leu Ala Gly Ala Gln Lys
 95             100                 105 cac att gat gct ggt gcg gaa aag gtt atc atc act gct cca tct tct    1467
His Ile Asp Ala Gly Ala Glu Lys Val Ile Ile Thr Ala Pro Ser Ser
110             115                 120                 125 gat gct cca atg ttt gtt gtt ggt gtt aac gaa aag gaa tac act cct    1515
Asp Ala Pro Met Phe Val Val Gly Val Asn Glu Lys Glu Tyr Thr Pro
                130                 135                 140 gac ttg aag att gtt tca aat gcc tca tgt acc acc aac tgc gtg gct    1563
Asp Leu Lys Ile Val Ser Asn Ala Ser Cys Thr Thr Asn Cys Val Ala
                145                 150                 155 aca tta gct aaa gtt gtt gac gat aac ttt gga att gaa tct ggg tta    1611
Thr Leu Ala Lys Val Val Asp Asp Asn Phe Gly Ile Glu Ser Gly Leu
            160                 165                 170 atg acc gct gtt cac gcc att act gct tcc caa aag atc gtc gat ggt    1659
Met Thr Ala Val His Ala Ile Thr Ala Ser Gln Lys Ile Val Asp Gly
175                 180                 185 ccc tcc cac aag gac tgg aga ggt ggt aga acc gct tcc ggc aac att    1707
Pro Ser His Lys Asp Trp Arg Gly Gly Arg Thr Ala Ser Gly Asn Ile
190                 195                 200                 205 atc cca tca tca act ggt gct gct aag gct gtt ggt aag gtt ttg cca    1755
Ile Pro Ser Ser Thr Gly Ala Ala Lys Ala Val Gly Lys Val Leu Pro
                210                 215                 220 gct tta gct ggc aag cta acc ggt atg tct ata agg gtt cct act act    1803
Ala Leu Ala Gly Lys Leu Thr Gly Met Ser Ile Arg Val Pro Thr Thr
                225                 230                 235 gat gtt tcc gtt gct gat tta acc gtt aac tta aag act gct acc acc    1851
Asp Val Ser Val Ala Asp Leu Thr Val Asn Leu Lys Thr Ala Thr Thr
            240                 245                 250 tac cag gaa att tgc gct gct ata aag aag gct tct gaa ggt gaa tta    1899
Tyr Gln Glu Ile Cys Ala Ala Ile Lys Lys Ala Ser Glu Gly Glu Leu
        255                 260                 265 aag ggt att tta ggt tac act gaa gat gcc gtt gtt tca acc gac ttc    1947
Lys Gly Ile Leu Gly Tyr Thr Glu Asp Ala Val Val Ser Thr Asp Phe
270                 275                 280                 285 tta acc gat agc aga tcg tct atc ttc gat gcc aaa gct ggt atc tta    1995
Leu Thr Asp Ser Arg Ser Ser Ile Phe Asp Ala Lys Ala Gly Ile Leu
                290                 295                 300
```

```
tta acc cca acc ttc gtt aag cta atc tct tgg tac gat aac gaa tac    2043
Leu Thr Pro Thr Phe Val Lys Leu Ile Ser Trp Tyr Asp Asn Glu Tyr
            305                 310                 315 ggt tat tcc acc aga gtt gtt gac tta cta caa cat gtt gct tcc gcc    2091
Gly Tyr Ser Thr Arg Val Val Asp Leu Leu Gln His Val Ala Ser Ala
            320                 325                 330 taa atcttccaac ctaaattgcg aaatataagc aagcaaaaat tatatgtata          2144
 * tttgtcttcc attgcataag tctatctttc ctgagaaata acaaaaatat gttcttttcg   2204
agacacttaa gttttatttt tgcccttagt acaaggcatc catttgcagt tgctgcttac   2264
agccctgaag gctattgcat cagcccaatt ggaaacaagt atagcatact gatttgaggg   2324
tttaattatc tgtaatattc aagtacttat atgcgtagaa cctccaaata gcaacacgaa   2384
aatccatcat ccaacaatca aagatgtgga gcaggccaag caagatgata ttttctcggt   2444
ggtggcggtt tcaatttctg gggtgcgtta ttgtgtggct tgtaccttgc agggtaaacc   2504
ttcgccagca gttccagtgg tctcttcgac gaacaacagg ctgaaattcg gctgtttcag   2564
catggcttgt ttttcctcca tgggactagc gtagatttat ccccccagaa agtttctctt   2624
cttgaatatc tctggtaccg accactaact agattataga ttactgcgac atgttaaagc   2684
attgtcgggg tctttaagca tgctcaacca acaggttgcc tgaagagctg cgtactaacc   2744
tggaacaggg ttcacagaaa gagggcaacc cagaaaaaac actatttgtt aacccttata   2804
gtgaagagtg ggggtacaaa atctttgacc cgtactccac tacgcagtt ttgataaaca    2864 cttgcagatt acctaatttg gtatgtacaa tttctaggca tgggataagt atagctttta   2924
atccggaagg ttcggataaa tactgtgctg tgtgccaggc aaatgcgtcc cactggagaa   2984
aaaggtaaag ccgactaacc gaagacccac ctacaataaa tttaccgagc caccgaaaaa   3044
ctcacgttac tcaatatatg agtaatgtac tactataact atgtgtggaa tagaattgta   3104
ttgtatagta gctcagctt cttcctggta tacggtcgac tttagcctaa acacttgttg    3164
gttcagtgaa tacagcctga ttagactaaa aggtagaagg actataaagg tgtacatacg   3224
gaaatcctac tccccactta aatagacaaa accctctaa gtgttgtttc gacgtaaagc    3284
tttgtttact gacaagcctt ggcaccgatc ccccgggctg caggaattc                3333

<210> SEQ ID NO 2
<211> LENGTH: 4409
<212> TYPE: DNA
<213> ORGANISM: Pichia methanolica
<220> FEATURE:
<221> NAME/KEY: CDS
<222> LOCATION: (1733)...(2734)

<400> SEQUENCE: 2
cccgggggat cttattttct gcaagaactt aaccgaggga catgtcaaac caagcatact     60
gtaaaagaaa tagccgatgg tttatatata tatatacttg cgttagtaga aacagtttat    120
gcatgcatgg atgcaagaac tcagatatca ggttatcaag aaacatggag aaattcctaa    180
acagaaacgg aattaatccg aaattctcgg tctcccaaag aaaatagatg cacaagctaa    240
tacagcttgc taactagctt caactttcaa aaaaaattct aagctattga atattcatca    300
agataatagt ctatataaag atgtaaagtc attattattg ggatatataa acgtcctata    360
tattgctgaa atgttaggtg tatgtactga aaacaatcag tttgagttta ccagagagag    420
acgatggatc tacagatcaa tagagagaga ataagatgag aataagatga ttaatagtga    480
gaggtagtag ccactggcgg gaggatgaaa atatcccgga taaacttaga agaaattaa     540
```

```
ttacacgtat aggtaacatt tgttattgtc aatctcaga tcagttgatg cctggaacag      600
atcgacttat agatattatc agatcataat catgaggcga ggtgcgacta gtaccaggtg      660
atgatatatt gtttccggtt atttcaaata gttgacgtcg ttgtgtgatt gggaaggcgt      720
cggagtaaca gaaacagtaa cggtacaagc atcattatga gttgagggta tgtagggaag      780
cagttgtttg taagcatgtt tacaaatgca atgcatgtta cgattggact acaattaaat      840
ccgaatgtac ctatataacg tgttgtacgt gttgtgccgt aagtagcccg atactagatg      900
cttactacgt cactgatctg ttcggatctc agtccattca tgtgtcaaaa tagttagtag      960
ctaaggggga tacagggaag atgtttggta cgattatcgg agggatgtgt cttctgaggg     1020
gggaggagag agggcgtgta aggagtttgt ttgtttgttt gtttgttgag agaaggggg      1080 gagaagaggg ggtggtgggc tgatggcaat tgatatagag ggagagtgtg cgttaactgt     1140
ttagtgtggt ggcggtacgg ggtacactgt agaggggac attataatgg ttatgtgtat      1200
atgctgtata tatgaataca agtagggagt gactacacat tgcaattgat aatatgtgta     1260
tgtgtgcgca tcagtatata cactcggagg ttctgaaagc catcattgta ttggacgttt     1320
gaatggtatt agatgacttg ttgtactaga ggacggagaa tgggtgagtg aagcaatag     1380 ataataatgg aaagtttgct cggtggtgga cattggcccg gagtagtgat accgtcacct     1440
taaaattgca gttaggggat gatgctccgg ggcacgacct gccaactaat ttaatagtcg     1500
tctaacgctg gaacaggtgt tgttccacaa gtagatgagt tgttggttg gctggtcaaa      1560 tgctgccttg atccatcgtt ttatatataa agactcactt ctcctcctct tgttcaattg     1620
tttcacactc aactgcttct ccctttatctt ttttttttcc ctgtttattt ccccattgaa    1680
ctagatcaca tcttttcata ttacacactt ttatttatta taattacaca aa atg gct    1738
                                                             Met Ala
                                                              1 att aac gtt ggt att aac ggt ttc ggt aga atc ggt aga tta gtc ttg       1786
Ile Asn Val Gly Ile Asn Gly Phe Gly Arg Ile Gly Arg Leu Val Leu
        5                  10                  15 aga gtt gct tta tca aga aag gac atc aac att gtt gct gtc aat gat       1834
Arg Val Ala Leu Ser Arg Lys Asp Ile Asn Ile Val Ala Val Asn Asp
    20                  25                  30 cct ttc att gct gct gaa tac gct gct tac atg ttc aag tac gat tcc       1882
Pro Phe Ile Ala Ala Glu Tyr Ala Ala Tyr Met Phe Lys Tyr Asp Ser
35                  40                  45                  50 act cac ggt aag tac gcc ggc gaa gtt tcc agt gac ggt aaa tac tta       1930
Thr His Gly Lys Tyr Ala Gly Glu Val Ser Ser Asp Gly Lys Tyr Leu
                55                  60                  65 atc att gat ggt aag aag att gaa gtt ttc caa gaa aga gac cca gtt       1978
Ile Ile Asp Gly Lys Lys Ile Glu Val Phe Gln Glu Arg Asp Pro Val
            70                  75                  80 aac atc cca tgg ggt aaa gaa ggt gtc caa tac gtt att gac tcc act       2026
Asn Ile Pro Trp Gly Lys Glu Gly Val Gln Tyr Val Ile Asp Ser Thr
        85                  90                  95 ggt gtt ttc act acc ttg gct ggt gct caa aag cac att gat gcc ggt       2074
Gly Val Phe Thr Thr Leu Ala Gly Ala Gln Lys His Ile Asp Ala Gly
    100                 105                 110 gct gaa aag gtt atc atc act gct cca tct gct gat gct cca atg ttc       2122
Ala Glu Lys Val Ile Ile Thr Ala Pro Ser Ala Asp Ala Pro Met Phe
115                 120                 125                 130 gtt gtt ggt gtt aac gaa aag gaa tac act tct gac ttg aag att gtt       2170
Val Val Gly Val Asn Glu Lys Glu Tyr Thr Ser Asp Leu Lys Ile Val
                135                 140                 145
```

-continued

```
tct aac gct tca tgt acc acc aac tgt ttg gct cca tta gct aag gtt      2218
Ser Asn Ala Ser Cys Thr Thr Asn Cys Leu Ala Pro Leu Ala Lys Val
        150                 155                 160 gtt aac gac aac ttt ggt att gaa tca ggt tta atg acc act gtc cac      2266
Val Asn Asp Asn Phe Gly Ile Glu Ser Gly Leu Met Thr Thr Val His
            165                 170                 175 tcc att acc gct acc caa aag acc gtc gat ggt cca tca cac aag gac      2314
Ser Ile Thr Ala Thr Gln Lys Thr Val Asp Gly Pro Ser His Lys Asp
        180                 185                 190 tgg aga ggt ggt aga act gct tcc ggt aac att atc cca tca tct act      2362
Trp Arg Gly Gly Arg Thr Ala Ser Gly Asn Ile Ile Pro Ser Ser Thr
195                 200                 205                 210 ggt gct gct aag gct gtt ggt aag gtt tta cct gtc tta gct ggt aag      2410
Gly Ala Ala Lys Ala Val Gly Lys Val Leu Pro Val Leu Ala Gly Lys
                215                 220                 225 tta acc ggt atg tct tta aga gtt cct act acc gat gtt tcc gtt gtt      2458
Leu Thr Gly Met Ser Leu Arg Val Pro Thr Thr Asp Val Ser Val Val
            230                 235                 240 gat tta acc gtt aac tta aag act cca acc act tac gaa gct att tgt      2506
Asp Leu Thr Val Asn Leu Lys Thr Pro Thr Thr Tyr Glu Ala Ile Cys
        245                 250                 255 gct gct atg aag aag gct tct gaa ggt gaa tta aag ggt gtt tta ggt      2554
Ala Ala Met Lys Lys Ala Ser Glu Gly Glu Leu Lys Gly Val Leu Gly
    260                 265                 270 tac act gaa gac gct gtt gtt tcc act gat ttc tta acc gat aac aga      2602
Tyr Thr Glu Asp Ala Val Val Ser Thr Asp Phe Leu Thr Asp Asn Arg
275                 280                 285                 290 tca tct atc ttt gat gct aag gct ggt atc tta tta acc cca act ttc      2650
Ser Ser Ile Phe Asp Ala Lys Ala Gly Ile Leu Leu Thr Pro Thr Phe
                295                 300                 305 gtt aag tta atc tct tgg tac gat aac gaa tac ggt tac tcc acc aga      2698
Val Lys Leu Ile Ser Trp Tyr Asp Asn Glu Tyr Gly Tyr Ser Thr Arg
            310                 315                 320 gtt gtt gat tta cta caa cac gtt gct tcc gct taa atcttacaat           2744
Val Val Asp Leu Leu Gln His Val Ala Ser Ala *
        325                 330 ctagattgtg aagtataagt aagcaaaaat tatatatata tttgtctttc atagtataag    2804
tatagttttc atgagaaata cagataaaca acaaaaaata agttcttttt gaaaagttta    2864
gattttattc ttgaacttag taaaagcctt ccttttacag ctgcttactt acaaccttga    2924
aggctattgc ataagctcaa ttgaaaacga gtataatata ctgatttcaa ggtttaatta    2984
tctgtaattt tcaagtactt ccatacgtgg aaacctccca caattaacag caacacgaaa    3044
catccatcat ccaacaaccg agatgcggat taggcccgga gagataatat ttttcggtgt    3104
ggcggtggtt tcaactccga acgcagcgca gccaaaagca aacagatgat ttagtgaact    3164
cttcttatga tagattttg gctgattgag ttgatctgac ctgtgtggtt cgatcgaatt     3224
ctattgtgtt tgatgccctg gtagtggtgt gcttcatctt attgtgaagt gtgaatccta    3284
gcgattatgg catttggacg ccaactacta gctctgacgg tagtggcttc tacgaatgta    3344
acttacaatt ctgctcaatt cgaacatctt ttcagtaaga gaagttatat atgtatgtgt    3404
gtatgtgtat gtaaatatac ataaccgctt gtggggggtga ttttggttt gtactgatgt    3464 gaaactcagt gctatcggat gatgctgtca ccaacaacag ctgcttaacc ttcttttttac   3524 tattctgata cagaattagg aaagtttccg gatttgtgat gtgcggcttt ggttgccatt    3584
agtctccttt ttttggaggg aggagtgaag tggtgcgtta tgtgccctga tccaatggtt    3644
ttgaaagagg gagctaggga tagttaatgg gtagacctat gaacattgtg tattaatata    3704
```

-continued

```
ttgaaatata caaacataac ggctgaaaac agcaagaaat caaaaaggca caatttcaat    3764
ggtatataac ttcaataatg atagtaatag taatggtagt agttattaca ggaggaataa    3824
tatcaagaaa ggaaaactaa aagtacacca acgtattcag aaatacaaaa acagcgaaca    3884
aaatcgtcga ttagtaattc atatcatgat tgccatccaa acagctttct ttcattgaac    3944
tcacgagggc ttgcactatt ttccctgctt gatgagtaat ccatcatttc aaactcggtt    4004
gaacctgtag caccagaagc gccatttgac gtaattggcc ttgtaatttg ctgttgttgt    4064
tgggatatgt ttgattcatt ttggaaacgt tcatgatgcc ctcttttttt gttgtttgtt    4124
gttggtatcg gtgaattcga tctagatgca gaactgccac tattgttgtt attgccgttg    4184
ttcgcattat tgttatcgtc aaagtcaaag tcaagtaatg aagaccaag ggaagcatca     4244 acaccaaaat cattcaacat cagtaaatcc gagtacgact taatggtatc tgcctgaatc    4304
gttgcttgct gctgattatg ctgttgttgg ttttgttgtt gctgtttcgc agtcagttgg    4364
aaatgatcca ctagttctag agcggccgcc accgcggtgg agctc                   4409
```

```
<210> SEQ ID NO 3
<211> LENGTH: 3077
<212> TYPE: DNA
<213> ORGANISM: Pichia methanolica

<400> SEQUENCE: 3
```

```
cagctgctct gctccttgat tcgtaattaa tgttatcctt ttactttgaa ctcttgtcgg      60
tccccaacag ggattccaat cggtgctcag cgggatttcc catgaggttt ttgacaactt     120
tattgatgct gcaaaaactt ttttagccgg gtttaagtaa ctgggcaata tttccaaagg     180
ctgtgggcgt tccacactcc ttgcttttca taatctctgt gtattgtttt attcgcattt     240
tgattctctt attaccagtt atgtagaaag atcggcaaac aaaatatcaa cttttatctt     300
gaacgctgac ccacggtttc aaataactat cagaactcta tagctatagg ggaagtttac     360
tgcttgctta aagcggctaa aaagtgtttg gcaaattaaa aaagctgtga caagtaggaa     420
ctcctgtaaa gggccgattc gacttcgaaa gagcctaaaa acagtgacta ttggtgacgg     480
aaaattgcta aaggagtact agggctgtag taataaataa tggaacagtg gtacaacaat     540
aaaagaatga cgctgtatgt cgtagcctgc acgagtagct cagtggtaga gcagcagatt     600
gcaaatctgt tggtcaccgg ttcgatccgg tctcgggctt ccttttttgc tttttcgata     660
tttgcgggta ggaagcaagg tctagttttc gtcgtttcgg atggtttacg aaagtatcag     720
ccatgagtgt ttccctctgg ctacctaata tatttattga tcggtctctc atgtgaatgt     780
ttctttccaa gttcggcttt cagctcgtaa atgtgcaaga aatatttgac tccagcgacc     840
tttcagagtc aaattaattt tcgctaacaa tttgtgtttt tctggagaaa cctaaagatt     900
taactgataa gtcgaatcaa catctttaaa tcctttagtt aagatctctg cagcggccag     960
tattaaccaa tagcatattc acaggcatca catcggaaca ttcagaatgg actcgcaaac    1020
tgtcgggatt ttaggtggtg gccaacttgg tcgtatgatc gttgaagctg cacacagatt    1080
gaatatcaaa actgtgattc tcgaaaatgg agaccaggct ccagcaaagc aaatcaacgc    1140
tttagatgac catattgacg gctcattcaa tgatccaaaa gcaattgccg aattggctgc    1200
caagtgtgat gttttaaccg ttgagattga acatgttgac actgatgcgt tggttgaagt    1260
tcaaaaggca actggcatca aaatcttccc atcaccagaa actatttcat tgatcaaaga    1320
taaatacttg caaaaagagc atttgattaa gaatggcatt gctgttgccg aatccttgtag   1380
```

-continued

```
tgttgaaagt agcgcagcat ctttagaaga agttggtgcc aaatacggct tcccatacat    1440
gctaaaatct agaacaatgg cctatgacgg aagaggtaat tttgttgtca aagacaagtc    1500
atatatacct gaagctttga aagttttaga tgacaggccg ttatacgccg agaaatgggc    1560
tccattttca aaggagttag ctgttatggt tgtgagatca atcgatggcc aagtttattc    1620
ctacccaact gttgaaacca tccaccaaaa caacatctgt cacactgtct ttgctccagc    1680
tagagttaac gatactgtcc aaaagaaggc ccaaattttg gctgacaacg ctgtcaaatc    1740
tttcccaggt gctggtatct ttggtgttga atgttttta ttacaaaatg gtgacttatt    1800
agtcaacgaa attgccccaa gacctcacaa ttctggtcac tataccatcg acgcttgtgt    1860 caccctcgcaa tttgaagctc atgttagggc cattactggt ctacccatgc cgaagaactt    1920
cacttgtttg tcgactccat ctacccaagc tattatgttg aacgttttag gtggcgatga    1980
gcaaaacggt gagttcaaga tgtgtaaaag agcactagaa actcctcatg cttctgttta    2040
cttatacggt aagactacaa gaccaggcag aaaaatgggt cacattaata tagtttctca    2100
atcaatgact gactgtgagc gtagattaca ttacatagaa ggtacgacta acagcatccc    2160
tctcgaagaa cagtacacta cagattccat tccgggcact tcaagcaagc cattagtcgg    2220
tgtcatcatg ggttccgatt cggacctacc agtcatgtct ctaggttgta atatattgaa    2280
gcaatttaac gttccatttg aagtcactat cgtttccgct catagaaccc cacaaagaat    2340
ggccaagtat gccattgatg ctccaaagag agggttgaag tgcatcattg ctggtgctgg    2400
tggtgccgct catttaccgg gaatggttgc ggcgatgacg ccgctgcctg ttattggtgt    2460
ccctgttaaa ggctctactt tggatggtgt tgattcacta cactccatcg ttcaaatgcc    2520
aagaggtatt cctgttgcta ctgtggctat taacaatgct actaacgctg ccttgctagc    2580
tatcacaatc ttaggtgccg gcgatccaaa tacttgtctg caatggaagt ttatatgaac    2640 aatatgaaa atgaagtttt gggcaaggct gaaaaattgg aaaatggtgg atatgaagaa    2700
tacttgagta catacaagaa gtagaacctt ttatatttga tatagtactt actcaaagtc    2760
ttaattgttc taactgttaa tttctgcttt gcatttctga aagtttaag acaagaaatc    2820 ttgaaatttc tagttgctcg taagaggaaa cttgcattca ataacatta acaataaatg    2880 acaataatat attatttcaa cactgctata tggtagtttt ataggtttgg ttaggatttg    2940
agatattgct agcgcttatc attatcctta attgttcatc gacgcaaatc gacgcatttc    3000
cacaaaaatt ttccgaacct gttttcact tctccagatc ttggtttagt atagcttttg    3060
acacctaata cctgcag                                                    3077
```

```
<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer ZC11,356

<400> SEQUENCE: 4
ttacatgttc aagtacgat                                                    19

<210> SEQ ID NO 5
<211> LENGTH: 18
<212> TYPE: DNA
<213> ORGANISM: Artificial Sequence
<220> FEATURE:
<223> OTHER INFORMATION: Oligonucleotide primer ZC11,357

<400> SEQUENCE: 5
```

```
tgatttcatc gtaagtgg                                              18

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer ZC11,733

<400> SEQUENCE: 6
atcccatggg gtaaagaagg                                            20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer ZC11,734

<400> SEQUENCE: 7
ataccggtta acttaccagc                                            20

<210> SEQ ID NO 8
<211> LENGTH: 55
<212> TYPE: DNA
<213> ORGANISM: Artificial Sequence
<220> FEATURE:
<223> OTHER INFORMATION: Oligonucleotide primer ZC19,334

<400> SEQUENCE: 8
ccatgattac gccaagctag cggccgcaat ttttaagaaa tccgattgga tagtg      55

<210> SEQ ID NO 9
<211> LENGTH: 64
<212> TYPE: DNA
<213> ORGANISM: Artificial Sequence
<220> FEATURE:
<223> OTHER INFORMATION: Oligonucleotide primer ZC19,333

<400> SEQUENCE: 9
gtaaaaatag aaggaaatct cattcttttg aattcaaata aataaaagtg ggttctatga  60
aaac                                                              64

<210> SEQ ID NO 10
<211> LENGTH: 12
<212> TYPE: DNA
<213> ORGANISM: Artificial Sequence
<220> FEATURE:
<223> OTHER INFORMATION: engineered sequence

<400> SEQUENCE: 10
gaattcaaaa ga                                                    12

<210> SEQ ID NO 11
<211> LENGTH: 17
<212> TYPE: DNA
<213> ORGANISM: Artificial Sequence
<220> FEATURE:
<223> OTHER INFORMATION: Oligonucleotide primer ZC9118

<400> SEQUENCE: 11
acctcccagt aagcctt                                               17

<210> SEQ ID NO 12
```

```
<211> LENGTH: 17
<212> TYPE: DNA
<213> ORGANISM: Artificial Sequence
<220> FEATURE:
<223> OTHER INFORMATION: Oligonucleotide primer ZC9464
<221> NAME/KEY: misc_feature
<222> LOCATION: (1)...(17)
<223> OTHER INFORMATION: n = A,T,C or G

<400> SEQUENCE: 12
ttyggnaart tygaygg                                                    17

<210> SEQ ID NO 13
<211> LENGTH: 421
<212> TYPE: DNA
<213> ORGANISM: Pichia methanolica
<220> FEATURE:
<221> NAME/KEY: CDS
<222> LOCATION: (2)...(421)

<400> SEQUENCE: 13
```

|   |   |   |   |   |   |   |   |   |   |   |   |   |   |   |   |   |
|---|---|---|---|---|---|---|---|---|---|---|---|---|---|---|---|---|
| g | gaa | ggt | aac | gtt | tct | cag | gat | act | tta | gct | tta | ggt | gat | tta | gtt | att | 49 |
|   | Glu | Gly | Asn | Val | Ser | Gln | Asp | Thr | Leu | Ala | Leu | Gly | Asp | Leu | Val | Ile |   |
|   | 1 |   |   |   | 5 |   |   |   |   | 10 |   |   |   |   | 15 |   |   |

```
cca aaa caa gac ttt gcc gaa gct act tct gag cca ggt tta gca ttc       97
Pro Lys Gln Asp Phe Ala Glu Ala Thr Ser Glu Pro Gly Leu Ala Phe
        20                  25                  30 gca ttt ggt aaa ttt gat ggt att tta ggt tta gct tac gat agc att     145
Ala Phe Gly Lys Phe Asp Gly Ile Leu Gly Leu Ala Tyr Asp Ser Ile
    35                  40                  45 tcg gtc aac aag att gtt cct cct att tat aat gct tta aac ttg ggt     193
Ser Val Asn Lys Ile Val Pro Pro Ile Tyr Asn Ala Leu Asn Leu Gly
50                  55                  60 tta tta gat gaa cct caa ttt gcc ttc tac cta ggt gat act aac acc     241
Leu Leu Asp Glu Pro Gln Phe Ala Phe Tyr Leu Gly Asp Thr Asn Thr
 65                  70                  75                  80 aat gaa gaa gat ggt ggt ctt gcc act ttt ggt ggt gtt gat gag tcc     289
Asn Glu Glu Asp Gly Gly Leu Ala Thr Phe Gly Gly Val Asp Glu Ser
                85                  90                  95 aag tat act ggt aaa gtt aca tgg tta cca gtc aga aga aag gct tac     337
Lys Tyr Thr Gly Lys Val Thr Trp Leu Pro Val Arg Arg Lys Ala Tyr
            100                 105                 110 tgg gaa gtt tca tta gac ggt att tca tta ggt gat gaa tac gcg cca     385
Trp Glu Val Ser Leu Asp Gly Ile Ser Leu Gly Asp Glu Tyr Ala Pro
        115                 120                 125 tta gaa ggc cat gga gct gcc att gat aca ggt acc                     421
Leu Glu Gly His Gly Ala Ala Ile Asp Thr Gly Thr
    130                 135                 140

<210> SEQ ID NO 14
<211> LENGTH: 140
<212> TYPE: PRT
<213> ORGANISM: Pichia methanolica

<400> SEQUENCE: 14

Glu Gly Asn Val Ser Gln Asp Thr Leu Ala Leu Gly Asp Leu Val Ile
1               5                   10                  15

Pro Lys Gln Asp Phe Ala Glu Ala Thr Ser Glu Pro Gly Leu Ala Phe
            20                  25                  30

Ala Phe Gly Lys Phe Asp Gly Ile Leu Gly Leu Ala Tyr Asp Ser Ile
        35                  40                  45

Ser Val Asn Lys Ile Val Pro Pro Ile Tyr Asn Ala Leu Asn Leu Gly
    50                  55                  60
```

```
Leu Leu Asp Glu Pro Gln Phe Ala Phe Tyr Leu Gly Asp Thr Asn Thr
 65                  70                  75                  80

Asn Glu Glu Asp Gly Gly Leu Ala Thr Phe Gly Gly Val Asp Glu Ser
                 85                  90                  95

Lys Tyr Thr Gly Lys Val Thr Trp Leu Pro Val Arg Arg Lys Ala Tyr
            100                 105                 110

Trp Glu Val Ser Leu Asp Gly Ile Ser Leu Gly Asp Glu Tyr Ala Pro
            115                 120                 125

Leu Glu Gly His Gly Ala Ala Ile Asp Thr Gly Thr
        130                 135                 140

<210> SEQ ID NO 15
<211> LENGTH: 17
<212> TYPE: DNA
<213> ORGANISM: Artificial Sequence
<220> FEATURE:
<223> OTHER INFORMATION: Oligonucleotide primer ZC9126

<400> SEQUENCE: 15
atgtcaacac atttacc                                                  17

<210> SEQ ID NO 16
<211> LENGTH: 17
<212> TYPE: DNA
<213> ORGANISM: Artificial Sequence
<220> FEATURE:
<223> OTHER INFORMATION: Oligonucleotide primer ZC9741
<221> NAME/KEY: misc_feature
<222> LOCATION: (1)...(17)
<223> OTHER INFORMATION: n = A,T,C or G

<400> SEQUENCE: 16
cayggnacnc aytgygc                                                  17

<210> SEQ ID NO 17
<211> LENGTH: 368
<212> TYPE: DNA
<213> ORGANISM: Pichia methanolica
<220> FEATURE:
<221> NAME/KEY: CDS
<222> LOCATION: (1)...(366)
<221> NAME/KEY: misc_feature
<222> LOCATION: (1)...(368)
<223> OTHER INFORMATION: n = A,T,C or G

<400> SEQUENCE: 17 ggg tcc gna cnc atg gtg ttt cta aga att gcc cac att gtt gcc gtc    48
Gly Ser Xaa Xaa Met Val Phe Leu Arg Ile Ala His Ile Val Ala Val
 1               5                  10                  15 aaa gtt tta aga tct aac ggt tca ggt tct atg ccc gat gtt gtc aag    96
Lys Val Leu Arg Ser Asn Gly Ser Gly Ser Met Pro Asp Val Val Lys
             20                  25                  30 ggt gtt gaa tat gct ccc aat gct cac ctt gcg gaa gcc aag gct aac   144
Gly Val Glu Tyr Ala Pro Asn Ala His Leu Ala Glu Ala Lys Ala Asn
         35                  40                  45 aag agt ggt ttt aaa ggt tct acc gcg aac atg tca tta ggt ggt ggt   192
Lys Ser Gly Phe Lys Gly Ser Thr Ala Asn Met Ser Leu Gly Gly Gly
     50                  55                  60 aaa tct cca gct tta gat atg tct gtt aac gct cct gtt aaa gca ggt   240
Lys Ser Pro Ala Leu Asp Met Ser Val Asn Ala Pro Val Lys Ala Gly
 65                  70                  75                  80 tta cac ttt gcc gtt acc gct ggt aac gat aac act gat gca tgt aac   288
Leu His Phe Ala Val Thr Ala Gly Asn Asp Asn Thr Asp Ala Cys Asn
```

```
tat tct cca gcc act act gaa aat act gtc act gtt gtt gct tcc act      336
Tyr Ser Pro Ala Thr Thr Glu Asn Thr Val Thr Val Val Ala Ser Thr
            100                 105                 110 tta tct gat tcg aga gct gac atg tct aac tc                            368
Leu Ser Asp Ser Arg Ala Asp Met Ser Asn
        115                 120
```

```
<210> SEQ ID NO 18
<211> LENGTH: 122
<212> TYPE: PRT
<213> ORGANISM: Pichia methanolica
<220> FEATURE:
<221> NAME/KEY: VARIANT
<222> LOCATION: (1)...(122)
<223> OTHER INFORMATION: Xaa = Any Amino Acid

<400> SEQUENCE: 18
```

```
Gly Ser Xaa Xaa Met Val Phe Leu Arg Ile Ala His Ile Val Ala Val
1               5                   10                  15

Lys Val Leu Arg Ser Asn Gly Ser Gly Ser Met Pro Asp Val Val Lys
            20                  25                  30

Gly Val Glu Tyr Ala Pro Asn Ala His Leu Ala Glu Ala Lys Ala Asn
        35                  40                  45

Lys Ser Gly Phe Lys Gly Ser Thr Ala Asn Met Ser Leu Gly Gly Gly
    50                  55                  60

Lys Ser Pro Ala Leu Asp Met Ser Val Asn Ala Pro Lys Ala Gly
65                  70                  75                  80

Leu His Phe Ala Val Thr Ala Gly Asn Asp Asn Thr Asp Ala Cys Asn
                85                  90                  95

Tyr Ser Pro Ala Thr Thr Glu Asn Thr Val Thr Val Val Ala Ser Thr
            100                 105                 110

Leu Ser Asp Ser Arg Ala Asp Met Ser Asn
        115                 120
```

```
<210> SEQ ID NO 19
<211> LENGTH: 17
<212> TYPE: DNA
<213> ORGANISM: Artificial Sequence
<220> FEATURE:
<223> OTHER INFORMATION: Oligonucleotide primer ZC447

<400> SEQUENCE: 19
taacaatttc acacagg                                                    17

<210> SEQ ID NO 20
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 20
cgttgtaaaa cgacggcc                                                   18

<210> SEQ ID NO 21
<211> LENGTH: 39
<212> TYPE: DNA
<213> ORGANISM: Artificial Sequence
<220> FEATURE:
<223> OTHER INFORMATION: Oligonucleotide primer ZC9079

<400> SEQUENCE: 21
```

```
cagctgccta ggactagttt cctcttacga gcaactaga                              39
```

<210> SEQ ID NO 22
<211> LENGTH: 38
<212> TYPE: DNA
<213> ORGANISM: Artificial Sequence
<220> FEATURE:
<223> OTHER INFORMATION: Oligonucleotide primer ZC9080

<400> SEQUENCE: 22

```
tgatcaccta ggactagtga caagtaggaa ctcctgta                               38
```

US 6,348,331 B1

PICHIA METHANOLICA GLYCERALDEHYDE-3-PHOSPHATE DEHYDROGENASE 2 PROMOTER

This application claims the benefit of provisional application No. 60/152,744 filed on Sep. 8, 1999.

BACKGROUND OF THE INVENTION

Methylotrophic yeasts are those yeasts that are able to utilize methanol as a sole source of carbon and energy. Species of yeasts that have the biochemical pathways necessary for methanol utilization are classified in four genera, Hansenula, Pichia, Candida, and Torulopsis. These genera are somewhat artificial, having been based on cell morphology and growth characteristics, and do not reflect close genetic relationships (Billon-Grand, *Mycotaxon* 35:201–204, 1989; Kurtzman, *Mycologia* 84:72–76, 1992). Furthermore, not all species within these genera are capable of utilizing methanol as a source of carbon and energy. As a consequence of this classification, there are great differences in physiology and metabolism between individual species of a genus.

Methylotrophic yeasts are attractive candidates for use in recombinant protein production systems for several reasons. First, some methylotrophic yeasts have been shown to grow rapidly to high biomass on minimal defined media. Second, recombinant expression cassettes are genomically integrated and therefore mitotically stable. Third, these yeasts are capable of secreting large amounts of recombinant proteins. See, for example, Faber et al., *Yeast* 11:1331, 1995; Romanos et al., *Yeast* 8:423, 1992; Cregg et al., *Bio/Technology* 11:905, 1993; U.S. Pat. No. 4,855,242; U.S. Pat. No. 4,857,467; U.S. Pat. No. 4,879,231; and U.S. Pat. No. 4,929,555; and Raymond, U.S. Pat. Nos. 5,716,808, 5,736,383, 5,854,039, and 5,888,768.

Previously described expression systems for methylotrophic yeasts rely largely on the use of methanol-inducible transcription promoters. The use of methanol-induced promoters is, however, problematic as production is scaled up to commercial levels. The overall volume of methanol used during the fermentation process can be as much as 40% of the final fermentation value, and at 1000-liter fermentation scale and above the volumes of methanol required for induction necessitate complex and potentially expensive considerations.

There remains a need in the art for additional materials and methods to enable the use of methylotrophic yeasts for production of polypeptides of economic importance, including industrial enzymes and pharmaceutical proteins. The present invention provides such materials and methods as well as other, related advantages.

SUMMARY OF THE INVENTION

It is an object of the present invention to provide transcription promoter and terminator sequences for use in *Pichia methanolica*. It is a further object of the invention to provide materials and methods for obtaining constitutive expression of heterologous DNA in *P. methanolica*. It is also an object of the invention to provide methods for production of polypeptides in *P. methanolica*, which methods can be readily scaled up to industrial levels, and to provide materials that can be used within these methods. It is another object of the invention to provide materials and methods for obtaining constitutive transcription of heterologous DNA to produce recombinant proteins in *P. methanolica*.

Within one aspect, the present invention provides an isolated DNA molecule of up to 5000 nucleotides in length comprising nucleotide 93 to nucleotide 1080 of SEQ ID NO:1.

Within a second aspect of the invention there is provided a DNA construct comprising the following operably linked elements: a first DNA segment comprising at least a portion of the sequence of SEQ ID NO:1 from nucleotide 93 to nucleotide 1092, wherein the portion is a functional transcription promoter; a second DNA segment encoding a protein of interest other than a *Pichia methanolica* glyceraldehyde-3-phosphate dehydrogenase; and a third DNA segment comprising a transcription terminator. Within one embodiment, the first DNA segment is from 900 to 1500 nucleotides in length. Within another embodiment, the first DNA segment is from 900 to 1000 nucleotides in length. Within an additional embodiment, the first DNA segment is substantially free of *Pichia methanolica* glyceraldehyde-3-phosphate dehydrogenase gene coding sequence. The DNA construct may further comprise a selectable marker, preferably a *Pichia methanolica* gene, more preferably a *Pichia methanolica* ADE2 gene. The DNA construct may be a closed, circular molecule or a linear molecule. Within other embodiments, the DNA construct further comprises a secretory signal sequence, such as the *S. cerevisiae* alpha-factor pre-pro sequence, operably linked to the first and second DNA segments. Within additional embodiments, the third DNA segment comprises a transcription terminator of a *Pichia methanolica* AUG1 or GAP2 gene.

Within a third aspect of the invention there is provided a *Pichia methanolica* cell containing a DNA construct as disclosed above. Within one embodiment, the DNA construct is genomically integrated. Within a related embodiment, the DNA construct is genomically integrated in multiple copies. Within a further embodiment, the *P. methanolica* cell is functionally deficient in vacuolar proteases proteinase A and proteinase B.

Within a fourth aspect of the invention there is provided a method of producing a protein of interest comprising the steps of (a) culturing a *P. methanolica* cell as disclosed above whereby the second DNA segment is expressed and the protein of interest is produced, and (b) recovering the protein of interest from the cultured cell.

Within a fifth aspect of the invention there is provided a DNA construct comprising the following operably linked elements: a first DNA segment comprising a *Pichia methanolica* gene transcription promoter; a second DNA segment encoding a protein of interest other than a *Pichia methanolica* protein; and a third DNA segment comprising nucleotides 2095 to 2145 of SEQ ID NO:1.

These and other aspects of the invention will become evident upon reference to the following detailed description of the invention.

DETAILED DESCRIPTION OF THE INVENTION

The term "allelic variant" is used herein to denote an alternative form of a gene. Allelic variation is known to exist in populations and arises through mutation.

A "DNA construct" is a DNA molecule, either single- or double-stranded, that has been modified through human intervention to contain segments of DNA combined and juxtaposed in an arrangement not existing in nature.

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "functionally deficient" denotes the expression in a cell of less than 10% of an activity as compared to the level of that activity in a wild-type counterpart. It is preferred that the expression level be less than 1% of the activity in the wild-type counterpart, more preferably less than 0.01% as determined by appropriate assays. It is most preferred that the activity be essentially undetectable (i.e., not significantly above background). Functional deficiencies in genes can be generated by mutations in either coding or non-coding regions.

The term "gene" is used herein to denote a DNA segment encoding a polypeptide. Where the context allows, the term includes genomic DNA (with or without intervening sequences), cDNA, and synthetic DNA. Genes may include non-coding sequences, including promoter elements.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones.

"Operably linked", when referring to DNA segments, indicates that the segments are arranged so that they function in concert for their intended purposes, e.g., transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. Sequences within promoters that function in the initiation of transcription are often characterized by consensus nucleotide sequences. These promoter elements include RNA polymerase binding sites, TATA sequences, and transcription factor binding sites. See, in general, Watson et al., eds., *Molecular Biology of the Gene*, 4th ed., The Benjamin/Cummings Publishing Company, Inc., Menlo Park, Calif., 1987.

A "pro sequence" is a DNA sequence that commonly occurs immediately 5' to the mature coding sequence of a gene encoding a secretory protein. The pro sequence encodes a pro peptide that serves as a cis-acting chaperone as the protein moves through the secretory pathway.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are commonly defined in terms of their amino acid backbone structures; substituents such as carbohydrate groups are generally not specified, but may be present nonetheless.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway. A secretory peptide and a pro peptide may be collectively referred to as a pre-pro peptide.

All references cited herein are incorporated by reference in their entirety.

The present invention provides isolated DNA molecules comprising a *Pichia methanolica* glyceraldehyde-3-phosphate dehydrogenase (GAPDH) gene promoter. The invention also provides isolated DNA molecules comprising a *P. methanolica* GAPDH gene terminator. The promoter and terminator can be used within methods of producing proteins of interest, including proteins of pharmaceutical or industrial value.

The sequence of a DNA molecule comprising a *Pichia methanolica* glyceraldehyde-3-phosphate dehydrogenase (GAPDH) gene promoter, coding region, and terminator is shown in SEQ ID NO:1. The gene has been designated GAP2. Those skilled in the art will recognize that SEQ ID NO:1 represents a single allele of the *P. methanolica* GAP2 gene and that other functional alleles (allelic variants) are likely to exist, and that allelic variation may include nucleotide changes in the promoter region, coding region, or terminator region.

The partial sequence of a second *P. methanolica* glyceraldehyde-3-phosphate dehydrogenase gene, designated GAP1, is shown in SEQ ID NO:2.

Within SEQ ID NO:1, the GAPDH open reading frame begins with the methionine codon (ATG) at nucleotides 1093–1095. The transcription promoter is located upstream of the ATG. Gene expression experiments showed that a functional promoter was contained within the ca. 1000 nucleotide 5'-flanking region of the GAP2 gene.

Preferred portions of the sequence shown in SEQ ID NO:1 for use within the present invention as transcription promoters include segments comprising at least 900 contiguous nucleotides of the 5' non-coding region of SEQ ID NO:1, and preferably comprising nucleotide 93 to nucleotide 1080 of the sequence shown in SEQ ID NO:1. Those skilled in the art will recognize that longer portions of the 5' non-coding region of the *P. methanolica* GAP2 gene can also be used. Promoter sequences of the present invention can thus include the sequence of SEQ ID NO:1 through nucleotide 1092 in the 3' direction and can extend to or beyond nucleotide 1 in the 5' direction. In general, the promoter used within an expression DNA construct will not exceed 1.5 kb in length, and will preferably not exceed 1.0 kb in length. In addition to these promoter fragments, the invention also provides isolated DNA molecules of up to about 3300 bp, as well as isolated DNA molecules of up to 5000 bp, wherein said molecules comprise the *P. methanolica* GAP2 promoter sequence.

As disclosed in more detail in the examples that follow, the sequence of SEQ ID NO:1 from nucleotide 93 to nucleotide 1080 provides a functional transcription promoter. However, additional nucleotides can be removed from either or both ends of this sequence and the resulting sequence tested for promoter function by joining it to a sequence encoding a protein, preferably a protein for which a convenient assay is readily available.

Within the present invention it is preferred that the GAP2 promoter be substantially free of GAP2 gene coding sequence, which begins with nucleotide 1093 in SEQ ID NO:1. As used herein, "substantially free" of GAP2 gene coding sequence means that the promoter DNA includes not more than 15 nucleotides of the GAP2 coding sequence, preferably not more than 10 nucleotides, and more preferably not more than 3 nucleotides. Within a preferred embodiment of the invention, the GAP2 promoter is provided free of coding sequence of the P. methanolica GAP2 gene. However, those skilled in the art will recognize that a GAP2 gene fragment that includes the initiation ATG (nucleotides 1093 to 1095) of SEQ ID NO:1 can be operably linked to a heterologous coding sequence that lacks an ATG, with the GAP2 ATG providing for intuition of translation of the heterologous sequence. Those skilled in the art will further recognize that additional GAP2 coding sequences can also be included, whereby a fusion protein comprising GAP2 and heterologous amino acid sequences is produced. Such a fusion protein may comprise a cleavage site to facilitate separation of the GAP2 and heterologous sequences subsequent to translation.

In addition to the GAP2 promoter sequence, the present invention also provides transcription terminator sequences derived from the 3' non-coding region of the P. methanolica GAP2 gene. A consensus transcription termination sequence (Chen and Moore, Mol. Cell. Biol. 12:3470–3481, 1992) is at nucleotides 2136 to 2145 of SEQ ID NO:1. Within the present invention, there are thus provided transcription terminator gene segments of at least about 50 bp, preferably at least 60 bp, more preferably at least 90 bp, still more preferably about 200 bp in length. The terminator segments of the present invention may comprise 500–1000 nucleotides of the 3' non-coding region of SEQ ID NO:1. These segments comprise the termination sequence disclosed above, and preferably have as their 5' termini nucleotide 2095 of SEQ ID NO:1. Those skilled in the art will recognize, however, that the transcription terminator segment that is provided in an expression vector can include at its 5' terminus the TAA translation termination codon at nucleotides 2092–2094 of SEQ ID NO:1 to permit the insertion of coding sequences that lack a termination codon.

Techniques for manipulating cloned DNA molecules and introducing exogenous DNA into a variety of host cells are well known in the art and are disclosed by, for example, Sambrook et al., *Molecular Cloning: A Laboratory Manual*, 2nd ed., Cold Spring Harbor Laboratory Press, Cold Spring Harbor, N.Y., 1989; Murray, ed., Gene Transfer and Expression Protocols, Humana Press, Clifton, N.J., 1991; Glick and Pasternak, *Molecular Biotechnology: Principles and Applications of Recombinant DNA*, ASM Press, Washington, D.C., 1994; Ausubel et al. (eds.), *Short Protocols in Molecular Biology*, 3rd edition, John Wiley and Sons, Inc., NY, 1995; Wu et al., *Methods in Gene Biotechnology*, CRC Press, New York, 1997. DNA vectors, including expression vectors, commonly contain a selectable marker and origin of replication that function in a bacterial host (e.g., *E. coli*) to permit the replication and amplification of the vector in a prokaryotic host. If desired, these prokaryotic elements can be removed from a vector before it is introduced into an alternative host. For example, such prokaryotic sequences can be removed by linearization of the vector prior to its introduction into a P. methanolica host cell.

Within certain embodiments of the invention, expression vectors are provided that comprise a first DNA segment comprising at least a portion of the sequence of SEQ ID NO:1 that is a functional transcription promoter operably linked to a second DNA segment encoding a protein of interest. When it is desired to secrete the protein of interest, the vector will further comprise a secretory signal sequence operably linked to the first and second DNA segments. The secretory signal sequence may be that of the protein of interest, or may be derived from another secreted protein, preferably a secreted yeast protein. A preferred such yeast secretory signal sequence is the *S. cerevisiae* alpha-factor (MFα1) pre-pro sequence (disclosed by Kurjan et al., U.S. Pat. No. 4,546,082 and Brake, U.S. Pat. No. 4,870,008).

Within other embodiments of the invention, expression vectors are provided that comprise a DNA segment comprising a portion of SEQ ID NO:1 that is a functional transcription terminator operably linked to an additional DNA segment encoding a protein of interest. Within one embodiment, the GAP2 promoter and terminator sequences of the present invention are used in combination, wherein both are operably linked to a DNA segment encoding a protein of interest within an expression vector.

Expression vectors of the present invention further comprise a selectable marker to permit identification and selection of P. methanolica cells containing the vector. Selectable markers provide for a growth advantage of cells containing them. The general principles of selection are well known in the art. The selectable marker is preferably a P. methanolica gene. Commonly used selectable markers are genes that encode enzymes required for the synthesis of amino acids or nucleotides. Cells having mutations in these genes cannot grow in media lacking the specific amino acid or nucleotide unless the mutation is complemented by the selectable marker. Use of such "selective" culture media ensures the stable maintenance of the heterologous DNA within the host cell. A preferred selectable marker of this type for use in P. methanolica is a P. methanolica ADE2 gene, which encodes phosphoribosyl-5-aminoimidazole carboxylase (AIRC; EC 4.1.1.21). See, Raymond, U.S. Pat. No. 5,736,383. The ADE2 gene, when transformed into an ade2 host cell, allows the cell to grow in the absence of adenine. The coding strand of a representative P. methanolica ADE2 gene sequence is shown in SEQ ID NO:3. The sequence illustrated includes 1006 nucleotides of 5' non-coding sequence and 442 nucleotides of 3' non-coding sequence, with the initiation ATG codon at nucleotides 1007–1009. Within a preferred embodiment of the invention, a DNA segment comprising nucleotides 407–2851 is used as a selectable marker, although longer or shorter segments could be used as long as the coding portion is operably linked to promoter and terminator sequences. In the alternative, a dominant selectable marker, which provides a growth advantage to wild-type cells, may be used. Typical dominant selectable markers are genes that provide resistance to antibiotics, such as neomycin-type antibiotics (e.g., G418), hygromycin B, and bleomycin/phleomycin-type antibiotics (e.g., Zeocin™; available from Invitrogen™ Corporation, San Diego, Calif.). A preferred dominant selectable marker for use in P. methanolica is the Sh bla gene, which inhibits the activity of Zeocin™.

The use of P. methanolica cells as a host for the production of recombinant proteins is disclosed in WIPO Publications WO 97/17450, WO 97/17451, WO 98/02536, and WO 98/02565; and U.S. Pat. Nos. 5,716,808, 5,736,383, 5,854, 039, and 5,736,383. Expression vectors for use in transforming *P. methanolica* will commonly be prepared as double-stranded, circular plasmids, which are preferably linearized prior to transformation. To facilitate integration of the expression vector DNA into the host chromosome, it is preferred to have the entire expression segment of the plasmid flanked at both ends by host DNA sequences (e.g., AUG1 3' sequences). Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette among individual isolates. It is therefore advantageous to screen a number of isolates for expression level prior to selecting a production strain. Isolates exhibiting a high expression level will commonly contain multiple integrated copies of the desired expression cassette. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

For production of secreted proteins, host cells having functional deficiencies in the vacuolar proteases proteinase A, which is encoded by the PEP4 gene, and proteinase B, which is encoded by the PRB1 gene, are preferred in order to minimize spurious proteolysis. Vacuolar protease activity (and therefore vacuolar protease deficiency) is measured using any of several known assays. Preferred assays are those developed for *Saccdaromyces cerevisiae* and disclosed by Jones, *Methods Enzymol.* 194:428–453, 1991. A preferred such assay is the APNE overlay assay, which detects activity of carboxypeptidase Y (CpY). See, Wolf and Fink, *J. Bact.* 123:1150–1156, 1975. Because the zymogen (pro) CpY is activated by proteinase A and proteinase B, the APNE assay is indicative of vacuolar protease activity in general. The APNE overlay assay detects the carboxypeptidase Y-mediated release of β-naphthol from N-acetyl-phenylalanine-p-naphthyl-ester (APNE), which results in the formation of an isoluble red dye by the reaction of the β-naphthol with the diazonium salt Fast Garnet GBC. Cells growing on assay plates (YEPD plates are preferred) at room temperature are overlayed with 8 ml R×M. R×M is prepared by combining 0.175 g agar, 17.5 ml $H_2O$, and 5 ml 1 M Tris-HCl pH 7.4, microwaving the mixture to dissolve the agar, cooling to ~55° C., adding 2.5 ml freshly made APNE (2 mg/ml in dimethylformamide) (Sigma Chemical Co., St. Louis, Mo.), and, immediately before assay, 20 mg Fast Garnet GBC salt (Sigma Chemical Co.). The overlay is allowed to solidify, and color development is observed. Wild-type colonies are red, whereas CPY deletion strains are white. Carboxypeptidase Y activity can also be detected by the well test, in which cells are distributed into wells of a microtiter test plate and incubated in the presence of N-benzoyl-L-tyrosine p-nitroanilide (BTPNA) and dimethylformamide. The cells are permeabilized by the dimethylformamide, and CpY in the cells cleaves the amide bond in the BTPNA to give the yellow product p-nitroaniline. Assays for CpY will detect any mutation that reduces protease activity so long as that activity ultimately results in the reduction of CpY activity.

*P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine, 0.006% L-leucine).

For large-scale culture, one to two colonies of a *P. methanolica* strain can be picked from a fresh agar plate (e.g, YEPD agar) and suspended in 250 ml of YEPD broth contained in a two-liter baffled shake flask. The culture is grown for 16 to 24 hours at 30° C. and 250 rpm shaking speed. Approximately 50 to 80 milliliters of inoculum are used per liter starting fermentor volume (5–8% v/v inoculum).

A preferred fermentation medium is a soluble medium comprising glucose as a carbon source, inorganic ammonia, potassium, phosphate, iron, and citric acid. As used herein, a "soluble medium" is a medium that does not contain visible precipitation. Preferably, the medium lacks phosphate glass (sodium hexametaphosphate). A preferred medium is prepared in deionized water and does not contain calcium sulfate. As a minimal medium, it is preferred that the medium lacks polypeptides or peptides, such as yeast extracts. However, acid hydrolyzed casein (e.g., casamino acids or amicase) can be added to the medium if desired. An illustrative fermentation medium is prepared by mixing the following compounds: $(NH_4)_2SO_4$ (1.5 grams/liter), $K_2HPO_4$ (2.60 grams/liter), $KH_2PO_4$ (9.50 grams/liter), $FeSO_4 \cdot 7H_2O$ (0.40 grams/liter), and citric acid (1.00 gram/liter). After adding distilled, deionized water to one liter, the solution is sterilized by autoclaving, allowed to cool, and then supplemented with the following: 60% (w/v) glucose solution (47.5 milliliters/liter), 10× trace metals solution (20.0 milliliters/liter), 1 M $MgSO_4$ (20.0 milliliters/liter), and vitamin stock solution (2.00 milliliters/liter). The 10× trace metals solution contains $FeSO_4 \cdot 7H_2O$ (100 mM), $CuSO_4 \cdot 5H_2O$ (2 mM), $ZnSO_4 \cdot 7H_2O$ (8 mM), $MnSO_4 \cdot H_2O$ (8 mM), $CoCl_2 \cdot 6H_2O$ (2 mM), $Na_2MoO_4 \cdot 2H_2O$ (1 mM), $H_3BO_3$ (8 mM), KI (0.5 mM) $NiSO_4 \cdot 6H_2O$ (1 mM), thiamine (0.50 grams/liter), and biotin (5.00 milligrams/liter). The vitamin stock solution contains inositol (47.00 grams/liter), pantothenic acid (23.00 grams/liter), pyrodoxine (1.20 grams/liter), thiamine (5.00 grams/liter), and biotin (0.10 gram/liter). Those of skill in the art can vary these particular ingredients and amounts. For example, ammonium sulfate can be substituted with ammonium chloride, or the amount of ammonium sulfate can be varied, for example, from about 11 to about 22 grams/liter.

After addition of trace metals and vitamins, the pH of the medium is typically adjusted to pH 4.5 by addition of 10% $H_3PO_4$. Generally, about 10 milliliters/liter are added, and no additional acid addition will be required. During fermentation, the pH is maintained between about 3.5 to about 5.5, or about 4.0 to about 5.0, depending on protein produced, by addition of 5 N $NH_4OH$.

An illustrative fermentor is a BIOFLO 3000 fermentor system (New Brunswick Scientific Company, Inc.; Edison, N.J.). This fermentor system can handle either a six-liter or a fourteen-liter fermentor vessel. Fermentations performed with the six-liter vessel are prepared with three liters of medium, whereas fermentations performed with the fourteen-liter vessel are prepared with six liters of medium. The fermentor vessel operating temperature is typically set to 30° C. for the course of the fermentation, although the temperature can range between 27–31° C. depending on the protein expressed. The fermentation is initiated in a batch mode. The glucose initially present is often used by approximately 10 hours elapsed fermentation time (EFT), at which time a glucose feed can be initiated to increase the cell mass. An illustrative glucose feed contains 900 milliliters of 60% (w/v) glucose, 60 milliliters of 50% (w/v) $(NH_4)_2SO_4$, 60 milliliters of 10x trace metals solution, and 30 milliliters of 1 M $MgSO_4$. Pichia methanolica fermentation is robust and requires high agitation, aeration, and oxygen sparging to maintain the percentage dissolved oxygen saturation above 30%. The percentage dissolved oxygen should not drop below 15% for optimal expression and growth. The biomass typically reaches about 30 to about 80 grams dry cell weight per liter at 48 hours EFT.

Proteins produced according to the present invention are recovered from the host cells using conventional methods. If the protein is produced intracellulary, the cells are harvested (e.g., by centrifugation) and lysed to release the cytoplasmic contents. Methods of lysis include enzymatic and mechanical disruption. The crude extract is then fractionated according to known methods, the specifics of which will be determined for the particular protein of interest. Secreted proteins are recovered from the conditioned culture medium using standard methods, also selected for the particular protein. See, in general, Scopes, *Protein Purification: Principles and Practice*, Springer-Verlag, New York, 1994.

The materials and methods of the present invention can be used to produce proteins of research, industrial, or pharmaceutical interest. Such proteins include enzymes, such as lipases, cellulases, and proteases; enzyme inhibitors, including protease inhibitors; growth factors such as platelet derived growth factor (PDGF), fibroblast growth factors (FGF), epidermal growth factor (EGF), vascular endothelial growth factors (VEGFs); glutamic acid decarboxylase (GAD); cytokines, such as erythropoietin, thrombopoietin, colony stimulating factors, interleukins, and interleukin antagonist; hormones, such as insulin, proinsulin, leptin, and glucagon; and receptors, including growth factor receptors, which can be expressed in truncated form ("soluble receptors") or as fusion proteins with, for example, immunoglobulin constant region sequences. DNAs encoding these and other proteins are known in the art. See, for example, U.S. Pat. Nos. 4,889,919; 5,219,759; 4,868,119; 4,968,607; 4,599,311; 4,784,950; 5,792,850; 5,827,734; 4,703,008; 4,431,740; and 4,762,791; and WIPO Publications WO 95/21920 and WO 96/22308.

It is particularly preferred to use the present invention to produce unglycosylated pharmaceutical proteins. Yeast cells, including *P. methanolica* cells, produce glycoproteins with carbohydrate chains that differ from their mammalian counterparts. Mammalian glycoproteins produced in yeast cells may therefore be regarded as "foreign" when introduced into a mammal, and may exhibit, for example, different pharmacokinetics than their naturally glycosylated counterparts.

The invention is further illustrated by the following, non-limiting examples.

EXAMPLES

Example 1

To clone the *P. metlanolica* GAP1 gene, sense (ZC11,356; SEQ ID NO:4) and antisense (ZC11,357; SEQ ID NO:5) PCR primers were designed from an alignment of the coding regions of GAPDH genes of *Saccharomyces cerevisiae, Kluyveromyces lactis*, and mouse. The primers were then used to amplify *P. methanolica* genomic DNA. An amplified sequence 608 bp long was recovered and was found to have 78.1% homology to the corresponding *S. cerevisiae* GAPDH gene sequence.

A *P. methanolica* genomic library was constructed in the vector pRS426 (Christianson et al., *Gene* 110:119–122, 1992), a shuttle vector comprising $2\mu$ and *S. cerevisiae* URA3 sequences, allowing it to be propagated in *S. cerevisiae*. Genomic DNA was prepared from strain CBS6515 according to standard procedures. Briefly, cells were cultured overnight in rich media, spheroplasted with zymolyase, and lysed with SDS. DNA was precipitated from the lysate with ethanol and extracted with a phenol/chloroform mixture, then precipitated with ammonium acetate and ethanol. Gel electrophoresis of the DNA preparation showed the presence of intact, high molecular weight DNA and appreciable quantities of RNA. The DNA was partially digested with Sau 3A by incubating the DNA in the presence of a dilution series of the enzyme. Samples of the digests were analyzed by electrophoresis to determine the size distribution of fragments. DNA migrating between 4 and 12 kb was cut from the gel and extracted from the gel slice. The size-fractionated DNA was then ligated to pRS426 that had been digested with Bam HI and treated with alkaline phosphatase. Aliquots of the reaction mixture were electroporated into *E. coli* MC1061 cells using an electroporator (Gene Pulser™; Bio-Rad Laboratories, Hercules, Calif.) as recommended by the manufacturer.

The library was screened by PCR using sense (ZC11,733; SEQ ID NO:6) and antisense (ZC11,734; SEQ ID NO:7) primers designed from the sequenced region of the *P. methanolica* GAPDH. The PCR reaction mixture was incubated for one minute at 94° C.; followed by 34 cycles of 94° C., one minute, 52° C., 45 seconds, 72° C., two minutes; and a termination cycle of 94° C., one minute, 54° C., one minute, 72° C., eleven minutes. Starting with 43 library pools, positive pools were identified and broken down to individual colonies. A single colony with a pRS426 plasmid containing the *P. methanolica* GAPDH gene as its insert was isolated. The orientation of the GAPDH gene and the length of the 5' and 3' flanking sequences in the insert were deduced by DNA sequencing (SEQ ID NO:2). This gene was designated GAP1.

Within SEQ ID NO:2, the GAPDH open reading frame begins with the methionine codon (ATG) at nucleotides 1733–1735. The transcription promoter is located upstream of the ATG. Gene expression experiments showed that a functional promoter was contained within the ca. 900 nucleotide 5'-flanking region of the GAP1 gene. Analysis of this promoter sequence revealed the presence of a number of sequences homologous to *Saccharomyces cerevisiae* promoter elements. These sequences include a concensus TATAAA box at nucleotides 1584 to 1591, a consensus Rap1p binding site (Graham and Chambers, *Nuc. Acids Res.* 22:124–130, 1994) at nucleotides 1355 to 1367, and potential Gcr1p binding sites (Shore, *Trends Genet.* 10:408–412, 1994) at nucleotides 1225 to 1229, 1286 to 1290, 1295 to 1299, 1313 to 1317, 1351 to 1354, 1370 to 1374, 1389 to 1393, and 1457 to 1461. A consensus transcription termination sequence (Chen and Moore, *Mol. Cell. Biol.* 12:3470–3481, 1992) was identified at nucleotides 2774 to 2787 of SEQ ID NO:2.

A plasmid containing the GAP1 gene, designated pGAPDH, has been deposited as an *E. coli* strain MC1061 transformant with American Type Culture Collection, Manassas, Va. under the terms of the Budapest Treaty. The deposited strain has been assigned the designation PTA-3 and a deposit date of May 4, 1999.

Example 2

Analysis of the *P. methanolica* genome by Southern blotting, using a PCR product from the coding region of the cloned GAP1 gene as a probe, indicated the presence of three independent GAPDH genes. Primers designed from the cloned sequence were used in various combinations to amplify *P. methanolica* genomic DNA. Positive pools were screened by PCR, and positives were re-amplified. PCR products were sequenced. Eight pools were found to be the same and corresponded to the previously cloned GAP1 gene. Two pools were distinct from the previously cloned gene and were identical to each other. Each of these two pools was plated and amplified by PCR through several rounds of sub-dividing. Sub-pools were streaked, and single colonies were picked for a final round of PCR screening. Positive clones were analyzed by PCR and restriction digestion. Each clone was found to be carried on a ~5 kb genomic segment. This gene, which was designated GAP2, was partially sequenced. The sequenced region included an open reading frame of 1002 base pairs (including the termination codon), a 5' non-coding region of 1092 base pairs, and a 3' non-coding region of 1239 base pairs (SEQ ID NO:1).

Example 3

A fragment of GAP2 DNA (SEQ ID NO:1) was isolated by PCR using two primers. Primer ZC19,334 (SEQ ID NO:8) contained 26 bp of vector flanking sequence and 25 bp corresponding to the 5' end of the first 1000 bp of the GAP2 promoter. Primer ZC19,333 (SEQ ID NO:9) contained 35 bp of the 3' end corresponding to *S. cerevisiae* alpha factor pre-pro sequence and 29 bp corresponding to the 3' end of the GAP2 promoter. The latter primer altered the 5' flanking sequence at nucleotides 1081–1092 to GAAT-TCAAAAGA (SEQ ID NO:10), resulting in the introduction of an EcoRI site. The PCR reaction conditions (five tubes in all) were: 20 cycles of 94° C. for 30 seconds, 55° C. for 30 seconds, and 72° C. for 1 minute; followed by a 4° C. soak. The five samples were combined into one tube and precipitated with 2 volumes of 100% ethanol. The resulting pellet was resuspended in 10 µl of water. The sample was serially diluted into TE (10 mM Tris, 2 mM EDTA) as 1:5, 1:25, and 1:125 dilutions. DNA concentration was estimated by running the PCR product on a 1% agarose gel. The expected approximately 1 kb fragment was seen. The remaining 8 µl of product was used for recombination as described below.

An expression plasmid named pTAP96, containing the *P. methanolica* GAP2 promoter, *S. cerevisiae* alpha factor pre-pro sequence, and a cDNA encoding leptin with an amino-terminal Glu-Glu affinity tag (Grussenmeyer et al., *Proc. Natl. Acad. Sci. USA* 82:7952–4, 1985), was constructed via homologous recombination using portions of the plasmids pTAP37 and pCZR189. Plasmid pTAP37 comprises a modified *P. methanolica* GAP1 promoter, the *P. methanolica* ADE2 selectable marker, the gene for ampicillin resistance in *E. coli*, the *S. cerevisiae* URA3 selectable marker, and the CEN-ARS of *S. cerevisiae*. pCZR189 comprises the *S. cerevisiae* alpha factor pre-pro sequence and the leptin coding sequence. One hundred microliters of competent yeast cells (*S. cerevisiae*) were combined with 7 µl of a mixture containing approximately 1 µg of NotI-cut pCZR189, 1 µg PCR product containing the GAP2 promoter as described above, and 100 ng of EcoRI-cut pTAP37 vector, and the mixture was transferred to a 0.2 cm electroporation cuvette. The yeast/DNA mixture was electropulsed at 0.75 kV (5 kV/cm), infinite ohms, 25 µF. To each cuvette was added 600 µl of 1.2 M sorbitol, and the yeast was then plated in two 300-µl aliquots onto two-URA D plates and incubated at 30° C.

After about 48 hours, the Ura$^+$ yeast transformants from a single plate were resuspended in 1 ml H$_2$O and spun briefly to pellet the yeast cells. The cell pellet was resuspended in 1 ml of lysis buffer (2% t-octylphenoxypolyethoxyethanol (Triton® X-100), 1% SDS, 100 mM NaCl, 10 mM Tris, pH 8.0, 1 mM EDTA). Five hundred microliters of the lysis mixture was added to a microcentrifuge tube containing 300 µl acid-washed glass beads and 200 µl phenol-chloroform, vortexed for 1 minute intervals two or three times, followed by a 5 minute spin in a microcentrifuge at maximum speed. Three hundred microliters of the aqueous phase was transferred to a fresh tube, and the DNA was precipitated with 600 µl ethanol, followed by centrifugation for 10 minutes at 4° C. The DNA pellet was resuspended in 100 µl H$_2$O.

Forty µl of electrocompetent *E. coli* cells (MC1061; Casadaban et al., *J. Mol. Biol.* 138, 179–207, 1980) were transformed by electroporation with 1 µl of the yeast DNA preparation at 2.0 kV, 25 µF, and 400 ohms. Following electroporation, 0.6 ml SOC (2% Bacto™ Tryptone (Difco™ Laboratories), 0.5% yeast extract (Difco™ Laboratories), 10 mM NaCl, 2.5 mM KCl, 10 mM MgCl$_2$, 10 mM MgSO$_4$, 20 mM glucose) was plated in one aliquot on LB+Amp plates (LB broth, 1.8% Bacto™ Agar (Difco™ Laboratories), 100 mg/L Ampicillin).

Cells harboring the correct expression construct for the GAP2 promoter driving synthesis of the alpha factor pre-pro/leptin fusion were screened via PCR using the same primers used to generate the GAP2 promoter. The PCR conditions were: 25 cycles of 94° C. for 30 seconds, 55° C. for 30 seconds, and 72° C. for 1 minute; followed 20 by a 4° C. soak. Two positive clones were identified on a 1% agarose gel and were subjected to sequence analysis. One of the correct clones was selected and designated pTAP96.

Plasmid pTAP96 DNA was prepared by anion exchange chromatography using a commercially available plasmid isolation kit (QIAGEN® Plasmid Maxi Kit; Qiagen® Inc., Valencia, Calif.). DNA was diagnostically cut with ScaI, producing the expected bands of approximately 1700 bp, 2250 bp doublet, and 6000 bp on a 1% gel. 1 µg of pTAP96 DNA was then cut with NotI and transformed into electrocompetent *P. methanolica* strain PMAD16 (disclosed in Example 4, below) as disclosed in U.S. Pat. No. 5,854,039. Transformants were selected on —ADE DS plates (Table 1).

Table 1

—ADE DS 0.056% -Ade -Trp -Thr powder 0.67% yeast nitrogen base without amino acids 2% D-glucose 0.5% 200× tryptophan, threonine solution 18.22% D-sorbitol.

—Ade -Trp -Thr powder powder made by combining 3.0 g arginine, 5.0 g aspartic acid, 2.0 g histidine, 6.0 g isoleucine, 8.0 g leucine, 4.0 g lysine, 2.0 g methionine, 6.0 g phenylalanine, 5.0 g serine, 5.0 g tyrosine, 4.0 g uracil, and 6.0 g valine (all L-amino acids).

200× tryptophan, threonine solution 3.0% L-threonine, 0.8% L-tryptophan in $H_2O$.

For plates, add 1.8% Bactom agar (Difco™ Laboratories).

White colonies, indicating the presence of the ADE2 gene, were patched onto -ADE plates, and cells were allowed to grow overnight. The cells were then replica plated onto YEPD plates and overlaid with a nitrocellulose membrane. The next day the filters were washed gently under deionized $H_2O$, then denatured in 1× Western denaturing buffer (625 mM Tris, 625 mM glycine, pH9.0, 5 mM β-mercaptoethanol) at 65° C. for 10 minutes. Filters were blocked for 30 minutes in TTBS (160 mM NaCl, 20 mM Tris pH7.4, 0.1% Tween 20) and 5% non-fat dry milk. The filters were then exposed to an anti-Glu-Glu tag antibody conjugated to horseradish peroxidase (5 μl of antibody diluted into 10 ml TTBS+5% non-fat dry milk) at room temperature for 1 hour. Filters were washed twice for 5 minutes in TTBS with no milk and rinsed briefly in water. The filters were screened using commercially available chemiluminescence reagents (ECL™ direct labelling kit; Amersham Corp., Arlington Heights, Ill.) as a 1:1 dilution, and the filters were immediately exposed to film. One clone produced a detectable signal.

Example 4

To generate a *P. methanolica* strain deficient for vacuolar proteases, the PEP4 and PRB1 genes were identified and disrupted. PEP4 and PRB1 sequences were amplified by PCR in reaction mixtures containing 100 pmol of primer DNA, 1× buffer as supplied (Boehringer Mannheim, Indianapolis, Ind.), 250 μM dNTPs, 1–100 pmol of template DNA, and 1 unit of Taq polymerase in a reaction volume of 100 μl. The DNA was amplified over 30 cycles of 94° C., 30 seconds; 50° C., 60 seconds; and 72° C., 60 seconds.

Using an alignment of PEP4 sequences derived from *S. cerevisiae* (Ammerer et al., *Mol. Cell. Biol.* 6:2490–2499, 1986; Woolford et al., *Mol. Cell. Biol.* 6:2500–2510, 1986) and *P. pastoris* (Gleeson et al., U.S. Pat. No. 5,324,660), several sense and antisense primers corresponding to conserved regions were designed. One primer set, ZC9118 (SEQ ID NO:11) and ZC9464 (SEQ ID NO:12) produced a PCR product of the expected size from genomic DNA, and this set was used to identify a genomic clone corresponding to the amplified region. DNA sequencing of a portion of this genomic clone (shown in SEQ ID NO:13) revealed an open reading frame encoding a polypeptide (SEQ ID NO:14) with 70% amino acid identity with proteinase A from *S. cerevisiae*.

Primers for the identification of *P. methanolica* PRB1 were designed on the basis of alignments between the PRB1 genes of *S. cerevisiae* (Moehle et al., *Mol. Cell. Biol.* 7:4390–4399, 1987), *P. pastoris* (Gleeson et al., U.S. Pat. No. 5,324,660), and *Kluyveromyces lactis* (Fleer et al., WIPO Publication WO 94/00579). One primer set, ZC9126 (SEQ ID NO:15) and ZC9741 (SEQ ID NO:16) amplified a ca. 400 bp fragment from genomic DNA (SEQ ID NO:17). This product was sequenced and found to encode a polypeptide (SEQ ID NO:18) with 70% amino acid identity with proteinase B from *S. cerevisiae*. The PRB primer set was then used to identify a genomic clone encompassing the *P. methanolica* PRB1 gene.

Deletion mutations in the *P. methanolica* PEP4 and PRB1 genes were generated using available restriction enzyme sites. The cloned genes were restriction mapped. The pep4Δ allele was created by deleting a region of approximately 500 bp between BamHI and NcoI sites and including nucleotides 1 through 393 the sequence shown in SEQ ID NO:13. The prb1Δ allele was generated by deleting a region of approximately 1 kbp between NcoI and EcoRV sites and including the sequence shown in SEQ ID NO:17. The cloned PEP4 and PRB1 genes were subcloned into pCZR139, a phagemid vector (pBluescript® II KS(+), Stratagene™, La Jolla, Calif.) that carried a 2.4 kb SpeI ADE2 insert, to create the deletions. In the case of PEP4 gene, the unique BamHI site in pCZR139 was eliminated by digestion, fill-in, and religation. The vector was then linearized by digestion with EcoRI and HindIII, and a ca. 4 kb EcoRI-HindIII fragment spanning the PEP4 gene was ligated to the linearized vector to produce plasmid pCZR142. A ca. 500 bp deletion was then produced by digesting pCZR142 with BamHI and NcoI, filling in the ends, and religating the DNA to produce plasmid pCZR143. The PRB1 gene (~5 kb XhoI-BamHI fragment) was subcloned into pCZR139, and an internal EcoRV-NcoI fragment, comprising the sequence shown in SEQ ID NO:17, was deleted to produce plasmid pCZR153.

Plasmid pCZR143 was linearized with Asp718, which cut at a unique site. The linearized plasmid was introduced into the *P. methanolica* PMAD11 strain (an ade2 mutant generated as disclosed in U.S. Pat. No. 5,736,383). Transformants were grown on -ADE DS (Table 1) to identify Ade$^+$ transformants. Two classes of white, Ade$^+$ transformants were analyzed. One class arose immediately on the primary transformation plate; the second became evident as rapidly growing white papillae on the edges of unstable, pink transformant colonies.

Southern blotting was used to identify transformants that had undergone the desired homologous integration event. 100 gl of cell paste was scraped from a 24–48 hour YEPD plate and washed in 1 ml water. Washed cells were resuspended in 400 μl of spheroplast buffer (1.2 M sorbitol, 10 mM Na citrate pH 7.5, 10 MM EDTA, 10 mM DTT, 1 mg/ml zymolyase 100T) and incubated at 37° C. for 10 minutes. Four hundred μl of 1% SDS was added, the cell suspension was mixed at room temperature until clear, 300 μl of 5 M potassium acetate was mixed in, and the mixture was clarified by microcentrifugation for 5 minutes. 750 μl of the clarified lysate was extracted with an equal volume of phenol:chloroform:isoamyl alcohol (25:24:1), 600 μl was transferred to a fresh tube, 2 volumes of 100% ethanol was added, and the DNA was precipitated by microcentrifug ion for 15 minutes at 4° C. The pellet was resuspended in 50 μl of TE (10 mM Tris pH 8.0, 1 mM EDTA) containing 100 μg/ml of RNase A. Ten μl of DNA (approximately 100 ng) was digested in 100 μl total volume with appropriate enzymes, precipitated with 200 μl ethanol, and resuspended in 10 μl of DNA loading dye. The DNA was separated in 0.7% agarose gels and transferred to nylon membranes (Nytran N+, Amersham™ Corp., Arlington Heights, Ill.) in a semi-dry blotting apparatus (BioRad Laboratories, Richmond, Calif.) as recommended by the manufacturer. Transferred DNA was denatured, neutralized, and cross-linked to the membrane with UV light using a Stratalinker (Stratagene™, La Jolla, Calif.). To identify strains with a tandem integration at PEP4, two probes were used. One was a 1400 bp EcoRI-HindIII fragment from the 3' end of PEP4. The second was a 2000 bp BamHI-EcoRI fragment from the 5' end of PEP4. Fragments were detected using chemiluminescence reagents (ECL™ direct labelling kit; Amersham™ Corp., Arlington Heights, Ill.).

Parent strains harboring a tandem duplication of the wild-type and deletion alleles of the gene were grown in YEPD broth overnight to allow for the generation of looped-out, Ade− strains. These cells were then plated at a density of 2000–5000 colonies per plate on adenine-limited YEPD plates, grown for 3 days at 30° C. and 3 days at room temperature. The shift to room temperature enhanced pigmentation of rare, pink, Ade colonies. Loop-out strains were consistently detected at a frequency of approximately one pink, Ade− colony per 10,000 colonies screened. These strains were screened for retention of the wild-type or mutant genes by Southern blotting or by PCR using primers that spanned the site of the deletion. An ade2-11 pep4Δ strain was designated PMAD15.

The PRB1 gene was then deleted from PMAD15 essentially as described above by transformation with plasmid pCZR153. Blots were probed with PCR-generated probes for internal portions of the PRB1 and ADE2 genes. The PRB1 probe was generated by subcloning a 2.6 kb ClaI-SpeI fragment of PRB1 into the phagemid vector pBluescript® II KS(+) to produce pCZR150, and amplifying the desired region by PCR using primers ZC447 (SEQ ID NO:19) and ZC976 (SEQ ID NO:20). The ADE2 probe was generated by amplifying the ADE2 gene in pCZR139 with primers ZC9079 (SEQ ID NO:21) and ZC9080 (SEQ ID NO:22). The resulting ade2-11 pep4Δ prb1Δ strain was designated PMAD16.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated DNA molecule of up to 5000 nucleotides in length comprising nucleotide 93 to nucleotide 1080 of SEQ ID NO:1.

2. A DNA construct comprising the following operably linked elements:
   a first DNA segment comprising at least a portion of the sequence of SEQ ID NO:1 from nucleotide 93 to nucleotide 1092, wherein said portion is a functional transcription promoter;
   a second DNA segment encoding a protein of interest other than a *Pichia methanolica* glyceraldehyde-3-phosphate dehydrogenase; and
   a third DNA segment comprising a transcription terminator.

3. The DNA construct of claim 2 wherein said first DNA segment is from 900 to 1500 nucleotides in length.

4. The DNA construct of claim 2 wherein the first DNA segment comprises nucleotide 93 to nucleotide 1080 of SEQ ID NO:1.

5. The DNA construct of claim 2 wherein the first DNA segment is substantially free of *Pichia methanolica* glyceraldehyde-3-phosphate dehydrogenase gene coding sequence.

6. The DNA construct of claim 2, further comprising a selectable marker.

7. The DNA construct of claim 2, further comprising a secretory signal sequence operably linked to the first and second DNA segments.

8. The DNA construct of claim 7, wherein the secretory signal sequence is the *S. cerevisiae* alpha-factor pre-pro sequence.

9. The DNA construct of claim 2 wherein said third DNA segment comprises a transcription terminator of a *Pichia methanolica* AUG1 or GAP2 gene.

10. The DNA construct of claim 9, wherein said terminator comprises nucleotides 2095 to 2145 of SEQ ID NO:1.

11. A *Pichia methanolica* cell containing the DNA construct of claim 2.

12. The *Pichia methanolica* cell of claim 11 wherein the DNA construct is genomically integrated.

13. The *Pichia methanolica* cell of claim 12 wherein the DNA construct is genomically integrated in multiple copies.

14. The *Pichia methanolica* cell of claim 11 wherein the first DNA segment is from 900 to 1500 nucleotides in length.

15. The *Pichia methanolica* cell of claim 11 wherein the first DNA segment comprises nucleotide 93 to nucleotide 1080 of SEQ ID NO:1.

16. The *Pichia methanolica* cell of claim 11, wherein the cell is functionally deficient in vacuolar proteases proteinase A and proteinase B.

17. A method of producing a protein of interest comprising:
   culturing the cell of claim 11 whereby the second DNA segment is expressed and the protein of interest is produced; and
   recovering the protein of interest from the cultured cell.

18. The method of claim 17 wherein the DNA construct is genomically integrated in multiple copies.

19. The method of claim 17, wherein the cell is deficient in vacuolar proteases proteinase A and proteinase B.

* * * * *